(12) United States Patent
Bennett et al.

(10) Patent No.: US 8,877,698 B2
(45) Date of Patent: Nov. 4, 2014

(54) METHOD AND COMPOSITION FOR DISINFECTING HARD SURFACES

(75) Inventors: Mark Timothy Bennett, West Milford, NJ (US); Andrew Francis Colurciello, Newburgh, NY (US); Caryn Oryniak, Hillsborough, NJ (US); Janette Kumyoung Suh, Westfiled, NJ (US); Laura Jean Vaccaro, Little Falls, NJ (US)

(73) Assignee: Reckitt Benckiser LLC, Parsippany, NJ (US)

( * ) Notice: Subject to any disclaimer, the term of this patent is extended or adjusted under 35 U.S.C. 154(b) by 156 days.

(21) Appl. No.: 12/783,982

(22) Filed: May 20, 2010

(65) Prior Publication Data
US 2010/0233098 A1 Sep. 16, 2010

Related U.S. Application Data

(63) Continuation of application No. 10/645,248, filed on Aug. 20, 2003, now Pat. No. 7,915,210, which is a continuation-in-part of application No. PCT/GB02/00357, filed on Jan. 25, 2002.

(30) Foreign Application Priority Data

Feb. 20, 2001 (GB) .................................. 0104153.2

(51) Int. Cl.
*C11D 3/20* (2006.01)
*A61L 2/18* (2006.01)
*A01N 31/02* (2006.01)
*A01N 31/04* (2006.01)

(52) U.S. Cl.
CPC . *A61L 2/18* (2013.01); *A01N 31/02* (2013.01); *A01N 31/04* (2013.01)

USPC ........... 510/182; 510/180; 510/181; 510/199; 510/382; 510/422; 424/405

(58) Field of Classification Search
USPC ......... 424/45–78, 405; 25/107; 510/392–405, 510/180, 181, 182, 199, 382, 422
See application file for complete search history.

(56) References Cited

U.S. PATENT DOCUMENTS 3,282,776 A * 11/1966 Kitzke et al. ..................... 424/45
4,695,453 A * 9/1987 Tuominen et al. ............. 514/724

(Continued)

FOREIGN PATENT DOCUMENTS

| EP | 0848907 | * | 6/1998 | ............. A01N 33/04 |
| WO | 0265838 A1 | | 1/2002 | |

(Continued)

OTHER PUBLICATIONS

International Search Report PCT/GB2013/051725 dated Sep. 2, 2013.

(Continued)

*Primary Examiner* — Tri V Nguyen
(74) *Attorney, Agent, or Firm* — Norris McLaughlin & Marcus PA

(57) ABSTRACT

Aqueous hard surface treatment compositions necessarily comprise an alcohol constituent selected from the group consisting of methanol, ethanol, n-propanol, isopropanol, n-butanol, benzyl alcohol, and mixtures thereof which alcohol constituent comprises from about 40 and 70 weight percent ("% wt") of the total weight of the composition of which it forms a part. Preferably however the alcohol constituent is present in an amount of from about 50% wt to about 70% wt, more preferably is present in amounts of from about 60% wt to about 70% wt.

17 Claims, 1 Drawing Sheet

(56) References Cited

U.S. PATENT DOCUMENTS

| | | | |
|---|---|---|---|
| 5,373,025 A | 12/1994 | Gay | |
| 5,403,587 A * | 4/1995 | McCue et al. | 424/736 |
| 5,780,064 A * | 7/1998 | Meisters et al. | 424/616 |
| 6,080,387 A * | 6/2000 | Zhou et al. | 424/45 |
| 6,136,771 A * | 10/2000 | Taylor et al. | 510/388 |
| 6,136,776 A * | 10/2000 | Dickler et al. | 510/439 |
| 6,344,218 B1 * | 2/2002 | Dodd et al. | 424/605 |
| 6,468,953 B1 * | 10/2002 | Hitchems et al. | 510/218 |
| 6,482,392 B1 * | 11/2002 | Zhou et al. | 424/45 |
| 7,182,537 B2 * | 2/2007 | Policicchio et al. | 401/138 |
| 2005/0019431 A1 | 1/2005 | Modak et al. | |
| 2005/0089496 A1 | 4/2005 | Lichtenberg et al. | |
| 2007/0020140 A1 | 1/2007 | Buhr et al. | |
| 2007/0134136 A1 | 6/2007 | Polyakov et al. | |

FOREIGN PATENT DOCUMENTS

| | | |
|---|---|---|
| WO | 03073857 A2 | 9/2003 |
| WO | 2008154395 A1 | 12/2008 |

OTHER PUBLICATIONS

International Search Report PCT/GB2013/051724 dated Sep. 2, 2013.

International Search Report PCT/GB2013/051722 dated Aug. 28, 2013.

International Search Report PCT/GB2013/051721 dated Aug. 28, 2013.

* cited by examiner

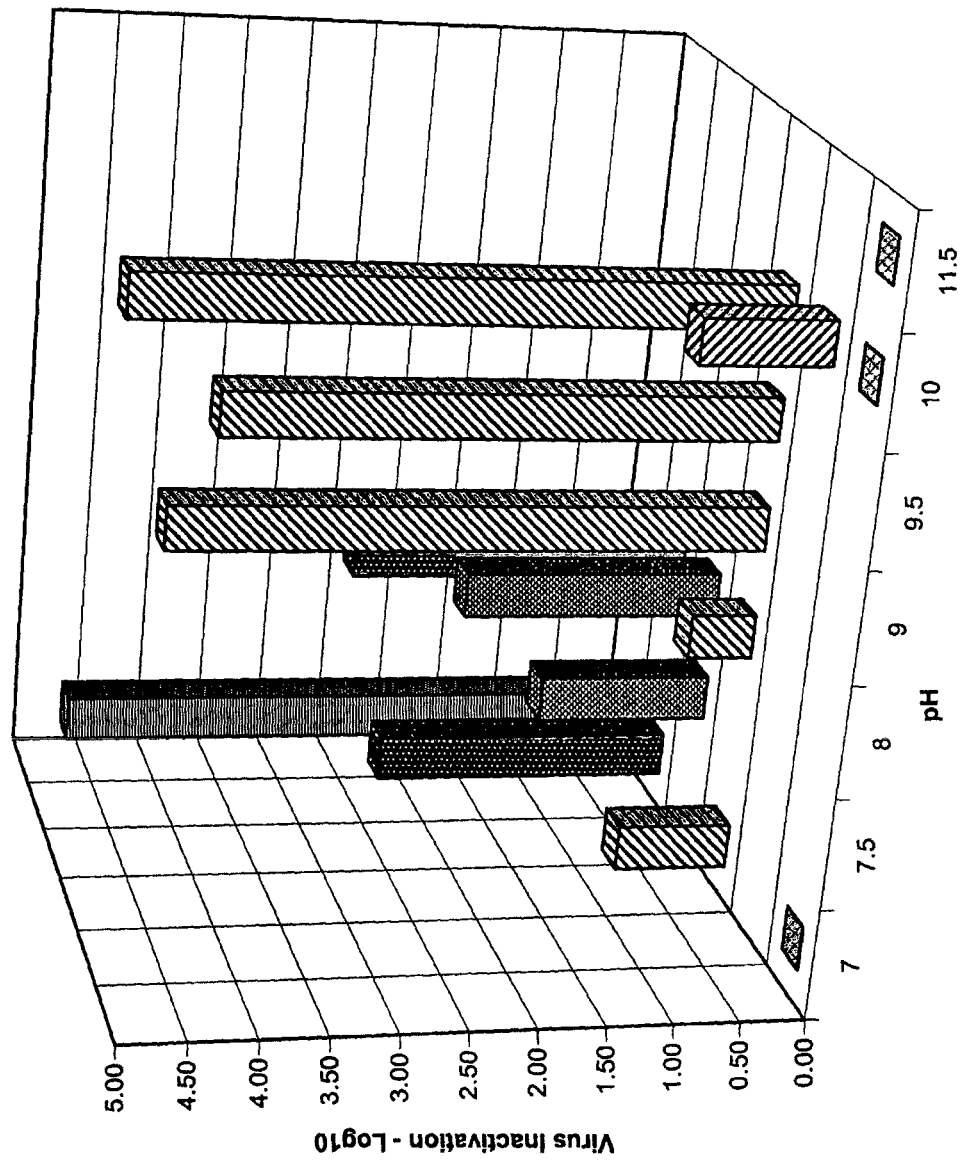

METHOD AND COMPOSITION FOR DISINFECTING HARD SURFACES

This application is a Continuation application of U.S. Ser. No. 10/645,248, now U.S. Pat. No. 7,915,210 filed Aug. 20, 2003 which in turn is a Continuation-In-Part application of PCT/GB02/00357 filed Jan. 25, 2002.

The present invention is directed compositions for the treatment of hard surfaces, as well as methods for disinfecting and/or sanitizing of such surfaces, particularly hard surfaces.

Microorganisms can usually be categorized into several general groups according to the innate resistance levels to a spectrum of physical or chemical germicidal agents (Manual of Clinical Microbiology, 5$^{th}$ edition, ed. A. Balows, ASM Press, Washington, D.C., p. 185 (1991). In order of decreasing resistance to germicidal agents the broad groups include: Bacterial spores, *Mycobacteria* (e.g. *Mycobacterium tuberculosis* var. *bovis*), Nonlipid or small viruses (e.g. poliovirus, coxsackie virus), Fungi (e.g. *Trichophyton* sp., *Candida* sp., *Aspergillis* sp.), Vegetative bacteria (e.g. *Staphylococcus aureus, Salmonella cholerasuis*), Lipid viruses (e.g. herpes simplex, HIV). From this scheme it can be presumed that activity against the more resistant organisms (e.g. *Mycobacterium tuberculosis* var. *bovis*, poliovirus) implies activity against the less resistant organisms (e.g. vegetative bacteria, lipid viruses).

It is generally known that ethanol can kill resistant organisms such as *Mycobacterium tuberculosis* var. *bovis* and poliovirus, but that high concentrations are needed (e.g. 70-90%). (*Disinfection, Sterilization, and Preservation*, Seymour S. Block, Lea & Febiger, Philadelphia, p. 197 (1991)) Prior studies have shown that ethanol, in concentrations of 63-70%, had little virucidal action against poliovirus. Other studies showed that a minimum concentration of 70% was required to inactivate this virus. While such high amounts of ethanol have been shown to be efficacious, such high amounts of ethanol, a known volatile organic compound ("VOC") poses an environmental problem. Recently there is substantial interest on the part of governmental regulators to reduce VOC (volatile organic compounds) content in products such as hard surface cleaning and disinfecting compositions.

In U.S. Pat. No. 5,180,749, there is disclosed an antimicrobial composition that includes up to only about 30 percent by weight ethanol. Those compositions also includes however, another germicidally active ingredient which is also a VOC, benzyl alcohol. Other prior art references also show the use of relatively low (e.g. about 50% by weight ethanol) but these compositions necessarily also include other active components, typically VOC. These other active components often are undesirable for a number of reasons, one of which is cost as well as a lack of efficacy against highly resistant organisms (e.g. poliovirus).

Accordingly, there is a real and continuing need in the art for improved hard surface treatment compositions which provide a cleaning or disinfecting benefit, (preferably both) and which overcomes one or more of the shortcomings of prior art hard surface cleaning compositions. Particularly there is a need for further improved hard surface cleaning and/or disinfecting compositions which are effective against a broad spectrum of microorganisms, especially those which are known to be highly resistant, and the same time which compositions feature a reduced VOC content in their compositions.

It is to these objects, as well as to other objects that the present invention is directed.

SUMMARY OF THE INVENTION

In accordance to a first aspect of the present invention, there is provided a hard surface treatment composition which comprises (preferably, consists essentially of) an alcohol constituent selected from the group consisting of methanol, ethanol, n-propanol, isopropanol, n-butanol, benzyl alcohol, and mixtures thereof which is present in an amount of from about 40 and 70 weight percent; an effective amount of a pH adjusting agent such that the pH range of the composition is from about 7.0 to about 13.0, wherein the amount of alcohol in the composition is inversely proportional to the pH of the composition; optionally, one or more constituents selected from the group consisting of antimicrobials, corrosion inhibitors, perfumes, perfume carriers, deodorants, organic solvents, surfactants, propellants, pH buffers, organic acids, fungicides, film-forming polymers, and anti-oxidants; and water, to 100 weight percent.

In accordance with a second aspect of the invention there is provided a hard surface treatment composition which comprises (preferably consists essentially of) an alcohol constituent selected from the group consisting of methanol, ethanol, n-propanol, isopropanol, n-butanol, benzyl alcohol, and mixtures thereof which is present in an amount of from about 40 and 70 weight percent; an effective amount of a pH adjusting agent such that the pH range of the composition is from about 7.0 to about 13.0, wherein the amount of alcohol in the composition is inversely proportional to the pH of the composition; a propellant; optionally, one or more constituents selected from the group consisting of antimicrobials, corrosion inhibitors, perfumes, perfume carriers, deodorants, organic solvents, surfactants, pH buffers, organic acids, fungicides, film-forming polymers, and anti-oxidants; and water, to 100 weight percent.

In accordance with a third aspect of the invention there are provided compositions according to the first or second aspects of the invention which necessarily further include an antimicrobial constituent.

According to a fourth aspect of the invention there are provided compositions according to the first, second or third aspects of the invention wherein the antimicrobial constituent is quaternary ammonium compound having antimicrobial properties or salt form thereof, but most desirably is a non-chloride ion containing quaternary ammonium antimicrobial having antimicrobial properties.

In accordance with a fifth and preferred aspect of the invention there are provided compositions according to any of the first through fourth aspects of the invention which compositions exhibit antimicrobial efficacy against gram positive type pathogenic bacteria such as *Staphylococcus aureus*, and/or gram negative type pathogenic bacteria such as *Salmonella choleraesuis* and/or *Pseudomonas aeruginosa,*

According to a sixth and particularly preferred aspect of the invention there are provided compositions according to any of the first through fifth aspects of the invention which compositions exhibit antimicrobial efficacy against Poliovirus (type 1).

According to a seventh aspect of the invention there are provided methods for the disinfecting treatment of hard surfaces wherein the presence of undesired microorganisms, e.g., gram positive type pathogenic bacteria or gram negative type pathogenic bacteria or viruses, particularly Poliovirus (type 1) is suspected, which process contemplates the step of applying an antimicrobially effective amount of a hard surface treatment composition described herein to the hard surfaces where the presence of undesired microorganisms is suspected.

According to an eighth aspect of the invention there are provided methods for the treatment of an ambient environment, particularly ambient air, which method contemplates the step of dispensing an effective amount of a composition according to any of the first through sixth aspects of the invention in an amount effective to exhibit antimicrobial efficacy against gram positive type pathogenic bacteria such as *Staphylococcus aureus*, and/or gram negative type pathogenic bacteria such as *Salmonella choleraesuis* and/or *Pseudomonas aeruginosa*.

In accordance with ninth preferred aspect of the invention there are provided compositions according to any of the first through fourth aspects of the invention which compositions exhibit antimicrobial efficacy against one or more of: *Salmonella choleraesuis, Staphylococcus aureus, Escherichia coli, Pseudomonas aeruginosa, Entercoccus hirae, Aspergillis niger, T. mentagrophytes*, Hepatitis A, Poliovirus, Coxsachievirus, rotavirus, and/or rhinovirus.

BRIEF DESCRIPTION OF THE DRAWING

FIG. 1 depicts the observed efficacy of different formulations of ethanol and $Na_4EDTA$ (1.5% $Na_4EDTA$ solution is 0.56% EDTA adjusted to pH with sodium citrate) at various pH levels against Poliovirus (type 1). The legend for FIG. 1 is as follows:

| | |
|---|---|
| ■ | 0% EtOH |
|  | 45% EtOH/1.5% $Na_4EDTA$ |
|  | 55% EtOH/1.5% $Na_4EDTA$ |
|  | 60% EtOH/1.5% $Na_4EDTA$ |
|  | 65% EtOH/1.5% $Na_4EDTA$ |
|  | 70% EtOH/1.5% $Na_4EDTA$ |

DETAILED DESCRIPTION AND PREFERRED EMBODIMENTS

The compositions according to the present invention necessarily comprise an alcohol constituent selected from the group consisting of methanol, ethanol, n-propanol, isopropanol, n-butanol, benzyl alcohol, and mixtures thereof which alcohol constituent comprises from about 40 and 70 weight percent ("% wt") of the total weight of the composition of which it forms a part. Preferably however the alcohol constituent is present in an amount of from about 50% wt to about 70% wt, more preferably is present in amounts of from about 60% wt to about 70% wt. Most preferably however, the alcohol constituent does not exceed 70% wt., and yet more preferably is present in an amount of up to 70% wt. According to certain particularly preferred embodiments of the invention the sole organic constituent present is selected from ethanol, isopropanol and mixtures thereof.

The compositions of the invention necessarily further include an effective amount of a pH adjusting agent such that the pH range of the composition is from about 7.0 to about 13.0. According to certain preferred aspects of the invention, the pH adjusting agent is present in a sufficient amount such that the compositions are in the pH range of from about 9 to about 12, more preferably from about 10 to about 12. According to further preferred aspects of the invention the pH adjusting agent is present in a sufficient amount such that the compositions are in the pH range in excess of 7 to about 10, preferably in excess of 7 to about 8.8.

While any material or composition which can provide function as a source of alkalinity in the inventive compositions may be used in the present invention, exemplary useful pH adjusting agents include alkali metal hydroxides such as lithium, sodium, potassium and calcium hydroxide; ammonium hydroxide; $Na_4EDTA$; tri- or tetraammonium ethylenediaminetetraacetate (ammonium EDTA); and tri- or tetrapotassium ethylenediaminetetraacetate (potassium EDTA). Alkali metal or hydrogen carbonates such as sodium carbonate or sodium hydrogen carbonate and alkali metal salts of borates or phosphates can also be used either alone, mixtures thereof, or in conjunction with the aforementioned pH adjusting agents. Particularly preferred pH adjusting agents include ammonium hydroxide, sodium hydroxide and tetrasodium ethylenediamine tetraacetic acid ($Na_4EDTA$). Desirably the inventive compositions contain significant amounts of $Na_4EDTA$ to adjust the pH although other compounds, e.g., sodium hydroxide, ammonium hydroxide can also contribute to the pH adjustment. The pH adjusting agent may be included in the inventive compositions in amounts which are found effective to achieve a target pH or target pH range. Generally, the inclusion of the pH adjusting agent in amounts of from about 0.01% wt. to about 5.0% wt., especially from about 0.1-2.5% wt. have been observed to be useful.

The pH can be adjusted to the desired level using one or more suitable pH adjusting agents, and surprisingly the inventors have found an inverse relationship between the alcohol level and the pH, both of which are believed to be factors which strongly influence the antimicrobial efficacy of the inventive compositions particularly against Poliovirus (type 1). For example, the inventors have found that, for example, a composition containing 45% wt. ethanol is effective against Poliovirus (type 1) when at a pH of 11.5 or greater Similar efficacy against Poliovirus (type1) is found with a 65% ethanol formulation at a pH of about 7.0. Thus, the higher the pH, the lower amount of alcohol, or the lower the pH, the higher amount of alcohol, have been found to be effective, and appear to define an inverse proportional relationship between these two technical aspects of the inventive compositions. Further examples, including especially preferred embodiments of inventive compositions are described with reference to one or more of the Examples. As will be seen in the comparative examples which follow, it is surprising that the alcohol containing compositions having a pH range from about 7.0 to about 13.0 provide good antimicrobial efficacy against poliovirus and other difficult pathogens since a high pH solution alone does not provide such a degree of antimicrobial efficacy.

As is noted above, the compositions according to the invention necessarily include a minor proportion of water, and water is added in quantum sufficient ("q.s.") in order to provide to 100% by weight of the inventive compositions. The water may be tap water, but is preferably distilled and is most preferably deionized water. If the water is tap water, it is preferably substantially free of any undesirable impurities such as organics or inorganics, especially minerals salts which are present in hard water which may thus undesirably interfere with the operation of the constituents present in the aqueous compositions according to the invention. Generally the content of water present in the inventive compositions ranges from about 30% wt. to about 55% wt.

The inventive compositions optionally, one or more constituents further selected from the group consisting of antimicrobials, corrosion inhibitors, perfumes, perfume carriers, deodorants, organic solvents, surfactants, propellants, pH buffers, organic acids, fungicides, film-forming polymers, and anti-oxidants. Such further optional may optionally be included in the compositions in order to provide aesthetic or other beneficial properties thereto, with the proviso that they be compatible with the other ingredients present within a composition of which they form a part. Such further optional constituents may be present in any effective amount, but typically the total amount of such optional constituents is not expected to exceed 10% wt., preferably not to exceed about 7% wt. of the inventive composition of which they form a part.

It is to be understood that in certain and preferred embodiments according to the present invention, e.g., according to the second and third aspects of the invention certain of the optional constituents are to be considered as necessary constituents in certain preferred embodiments of the invention.

The inventive compositions may comprise one or more antimicrobials which may be any of a number of known-art compounds or materials. By way of non-limiting example, useful antimicrobials include certain phenolic compounds such as o-phenylphenol, o-benzyl-p-chlorophenol and 4-tertamylphenol. Further exemplary useful antimicrobial agents include those described in U.S. Pat. No. 3,835,057 and U.S. Pat. No. 4,714,563 the contents of which are herein incorporated by reference. Particular antimicrobials that are useful include: 2,6-dimethyl-4-hydroxychlorobenzene; 3,4,4'-trichlorocarbanilide; 3-trifluoromethyl-4,4'-dichlorocarbanilide; 2,2'-dihydroxy-3,3',5,5',6,6'-hexachlorodiphenylmethane; 2,2'-dihydroxy-3,3',5,5'-tetrachlorodiphenylmethane; 2,2'-dihydroxy-3,3'-dibromo-5,5'-dichlorodiphenylmethane; 2-hydroxy-4,4'-dichlorodiphenylether; 2-hydroxy-3,5',4-tribromodiphenylether; and 1-hydroxy-4-methyl-6-(2.4.4-trimethylpentyl)-2(1H)pyridinone.

A class of particularly preferred antimicrobials which find use in the present inventive compositions include cationic surfactant which is found to provide a broad antibacterial or sanitizing function. Any cationic surfactant which satisfies these requirements may be used and are considered to be within the scope of the present invention, and mixtures of two or more cationic surface active agents, viz., cationic surfactants may also be used. Cationic surfactants are well known, and useful cationic surfactants may be one or more of those described for example in McCutcheon's Functional Materials, Vol. 2, 1998; Kirk-Othmer, Encyclopedia of Chemical Technology, 4th Ed., Vol. 23, pp. 481-541 (1997), the contents of which are herein incorporated by reference. These are also described in the respective product specifications and literature available from the suppliers of these cationic surfactants.

Examples of preferred cationic surfactant compositions useful in the practice of the instant invention are those which provide a germicidal effect to the concentrate compositions, and especially preferred are quaternary ammonium compounds and salts thereof, which may be characterized by the general structural formula:

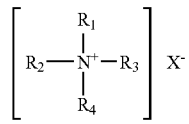

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

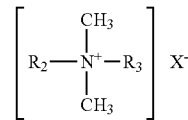

wherein $R_2$ and $R_3$ are the same or different $C_8$-$C_{12}$alkyl, or $R_2$ is $C_{12}$-$C_{16}$alkyl, $C_8$-$C_{18}$alkylethoxy, $C_8$-$C_{18}$alkylphenolethoxy and $R_3$ is benzyl, and X is a halide, for example chloride, bromide or iodide, or is a methosulfate anion. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Such useful quaternary compounds are available under the BARDAC®, BARQUAT®, HYAMINE®, LONZABAC®, and ONYXIDE® trademarks, which are more fully described in, for example, McCutcheon's Functional Materials (Vol. 2), North American Edition, 1998, as well as the respective product literature from the suppliers identified below. For example, BARDAC® 205M is described to be a liquid containing alkyl dimethyl benzyl ammonium chloride, octyl decyl dimethyl ammonium chloride; didecyl dimethyl ammonium chloride, and dioctyl dimethyl ammonium chloride (50% active) (also available as 80% active (BARDAC® 208M)); described generally in McCutcheon's as a combination of alkyl dimethyl benzyl ammonium chloride and dialkyl dimethyl ammonium chloride); BARDAC® 2050 is described to be a combination of octyl decyl dimethyl ammonium chloride/didecyl dimethyl ammonium chloride, and dioctyl dimethyl ammonium chloride (50% active) (also available as 80% active (BARDAC® 2080)); BARDAC® 2250 is described to be didecyl dimethyl ammonium chloride (50% active); BARDAC® LF (or BARDAC® LF-80), described as being based on dioctyl dimethyl ammonium chloride (BARQUAT® MB-50, MX-50, OJ-50 (each 50% liquid) and MB-80 or MX-80 (each 80% liquid) are each described as an alkyl dimethyl benzyl ammonium chloride; BARDAC® 4250 and BARQUAT® 4250Z (each 50% active) or BARQUAT® 4280 and BARQUAT 4280Z (each 80% active) are each described as alkyl dimethyl benzyl ammonium chloride/alkyl dimethyl ethyl benzyl ammonium chloride. Also, HYAMINE® 1622, described as diisobutyl phenoxy ethoxy ethyl dimethyl benzyl ammonium chloride (50% solution); HYAMINE® 3500 (50% actives), described as alkyl dimethyl benzyl ammonium chloride (also available as 80% active (HYAMINE® 3500-80)); and HYMAINE® 2389 described as being based on methyldodecylbenzyl ammonium chloride and/or methyldodecylxylene-bis-trimethyl ammonium chloride. (BARDAC®, BARQUAT® and HYAMINE® are presently commercially available from Lonza, Inc., Fairlawn, N.J.). BTC® 50 NF (or BTC® 65 NF) is described to be alkyl dimethyl benzyl ammonium chloride (50% active); BTC® 99 is described as didecyl dimethyl ammonium chloride (50% active); BTC® 776 is described to be myrisalkonium chloride (50% active); BTC® 818 is described as being octyl decyl dimethyl ammonium chloride, didecyl dimethyl ammonium chloride, and dioctyl dimethyl ammonium chloride (50% active) (available also as 80% active (BTC® 818-80%)); BTC® 824 and BTC® 835 are each described as being of alkyl dimethyl benzyl ammonium chloride (each 50% active); BTC® 885 is described as a combination of BTC® 835 and BTC® 818 (50% active) (available also as 80% active (BTC® 888)); BTC® 1010 is described as didecyl dimethyl ammonium chloride (50% active) (also available as 80% active (BTC® 1010-80)); BTC® 2125 (or BTC® 2125 M) is described as alkyl dimethyl benzyl ammonium chloride and alkyl dimethyl ethylbenzyl ammonium chloride (each 50% active) (also available as 80% active (BTC® 2125 80 or BTC® 2125 M)); BTC® 2565 is described as alkyl dimethyl benzyl ammonium chlorides (50% active) (also available as 80% active (BTC® 2568)); BTC® 8248 (or BTC® 8358) is described as alkyl dimethyl benzyl ammonium chloride (80% active) (also available as 90% active (BTC® 8249)); ONYXIDE® 3300 is described as non-chloride ion containing n-alkyl dimethyl benzyl ammonium saccharinate (95% active). (BTC® and ONYXIDE® are presently commercially available from Stepan Company, Northfield, Ill.) Polymeric quaternary ammonium salts based on these monomeric structures are also considered desirable for the present invention. One example is POLYQUAT®, described as being a 2-butenyldimethyl ammonium chloride polymer. Of these quaternary ammonium compounds preferred are those which are non-chloride ion containing compounds. A particularly preferred antimicrobial is ONYXIDE® 3300. This is a quaternary ammonium antimicrobial that is less corrosive than typical halogen based quaternary ammonium compounds. When added to the inventive compositions, the additional antimicrobial agent is generally present in an amount of from about 0.01% wt. to about 0.10% wt.

The inventive compositions may optionally include one or more corrosion inhibitors, which are preferred for use in inventive compositions which are supplied in a pressurized dispensing container, such as an aerosol container. Exemplary corrosion inhibitors include known art compounds and materials, e.g., mono- and triethanolamine, ammonium hydroxide, sodium molybdate and sodium benzoate, borates, silicates, as well as other corrosion inhibitors well known to those of ordinary skill in the art. While it may be included in any effective amount, when present, the corrosion inhibitor is advantageously present in an amount of from about 0.02% wt. to about 0.50% wt. of the composition, preferably from about 0.05-0.10% wt. Those of ordinary skill in the art will appreciate that if compositions of the present invention are prepared in a non-aerosol system, corrosions inhibitors will not be necessary when such compositions are placed in plastic bottles with trigger pumps sprays or squirt-type dispensers or impregnated into towelettes also commonly referred to as wipes.

The compositions according to the invention may optionally comprise one or more organic solvents. By way of non-limiting example exemplary useful organic solvents which may be included in the inventive compositions include those which are at least partially water-miscible such as alcohols (e.g., low molecular weight alcohols, such as, for example, ethanol, propanol, isopropanol, and the like), glycols (such as, for example, ethylene glycol, propylene glycol, hexylene glycol, and the like), water-miscible ethers (e.g. diethylene glycol diethylether, diethylene glycol dimethylether, propylene glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethylene glycol or propylene glycol (e.g. propylene glycol monomethyl ether acetate), and mixtures thereof. Glycol ethers having the general structure Ra-Rb-OH, wherein Ra is an alkoxy of 1 to 20 carbon atoms, or aryloxy of at least 6 carbon atoms, and Rb is an ether condensate of propylene glycol and/or ethylene glycol having from one to ten glycol monomer units. Of course, mixtures of two or more organic solvents may be used in the organic solvent constituent. One or more glycols are particularly useful in air sanitizer embodiments such as in accordance with the recited eighth aspect of the invention, especially triethylene glycol. The organic solvent(s), when present, may be included in any effective amount.

The inventive compositions may optionally, and in certain preferred embodiments may include one or more water soluble or water dispersible $C_1$-$C_6$ organic acids, particularly one or more selected from the group consisting of: citric acid, sorbic acid, acetic acid, boric acid, formic acid, maleic acid, adipic acid, lactic acid, malic acid, malonic acid, glycolic acid, and mixtures thereof. Each of these acids are water soluble, and comprises as least one carboxyl group (—COOH) in its structure. In certain embodiments according to the invention the presence of a minor amount of one or more such acids, especially citric acid, in amounts of up to 1% wt., preferably 0.01-0.5% wt, and most preferably from 0.05-0.5% wt. is preferred to be included in the inventive compositions, and in certain particularly preferred embodiments one or more such acids is an essential constituent.

The inventive compositions may include one or more pH buffers which may be included in any effective amount. The compositions according to the invention optionally but desirably include an amount of a pH adjusting agent or pH buffer composition. Such compositions include many which are known to the art and which are conventionally used. By way of non-limiting example pH adjusting agents include phosphorus containing compounds, monovalent and polyvalent salts such as of silicates, carbonates, and borates, certain acids and bases, tartrates and certain acetates. Further exemplary pH adjusting agents include mineral acids, basic compositions, and organic acids, which are typically required in only minor amounts. By way of further non-limiting example pH buffering compositions include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts. Desirably the compositions according to the invention include an effective amount of an organic acid and/or an inorganic salt form thereof which may be used to adjust and maintain the pH of the compositions of the invention to the desired pH range. Particularly useful is citric acid and metal salts thereof such as sodium citrate which are widely available and which are effective in providing these pH adjustment and buffering effects.

The inventive compositions may optionally include one or more perfume constituents. Any compound or material which provides a desirable scent or odor to the inventive compositions may be used. Exemplary useful perfumes include any water soluble, water dispersible as well as any non-water soluble fragrance substance or mixture of such substances including those which are naturally derived (i.e., obtained by extraction of flower, herb, blossom or plant), those which are artificially derived or produced (i.e., mixture of natural oils and/or oil constituents), and those which are synthetically produced substances (odiferous substances). Generally perfumes are complex mixtures or blends various organic compounds including, but not limited to, certain alcohols, aldehydes, ethers, aromatic compounds and varying amounts of essential oils such as from about 0 to about 85% by weight, usually from about 10 to about 70% by weight, the essential oils themselves being volatile odiferous compounds and also functioning to aid in the dissolution of the other components of the perfume. In the present invention, the precise composition of the perfume is of no particular consequence to cleaning performance so long as it may be effectively included as a constituent of the compositions, and have a pleasing fragrance. For those compositions which are intended to be used in a domestic environment, the perfume, as well as the other ingredients used in making up compositions of the invention should be cosmetically acceptable, i.e., feature low toxicity or no toxicity, hypoallergenic character, etc. Perfumes, and when necessary perfume carriers, when present, may be included in any effective amount.

The inventive compositions may also optionally include a compound or material which provides a deodorizing effect, such as N-alkyl-N-ethylmorpolinium ethyl sulfate; such compounds or materials may be included in any deodorizing effective amount.

The inventive compositions may also include one or more surfactants selected from nonionic, anionic, cationic surfactants, zwitterionic and amphoteric surfactants in effective amounts. Generally the inventors have found that the inclusion of minor amounts of one or more surfactants may improve surface wetting of the inventive composition and to improve evenness of distribution of the inventive composition on a hard surface as well as its contact therewith. Such further optional surfactants generally need be present only in small amounts, e.g., up to about 2% wt., preferably not more than 1% wt, and most preferably in amount not to exceed 0.5% wt. By way of non-limiting example, such further surfactants include (1) alkyl sulfonates and sulfates wherein the alkyl is straight or branched and has from about 8 to about 24 carbon atoms and the cation is water-soluble, e.g., alkali metal and ammonium;

(2 (preferred)) fluorinated surfactants such as, for example, anionic, nonionic, cationic and amphoteric fluorosurfactants marketed by E.I. Dupont de Nemours and Company under the trademark ZONYL® e.g. ZONYL® FSK, an amphoteric fluorosurfactant, ZONYL® FSN and ZONYL® FSO, fluorosurfactants, ZONYL® FSJ, an anionic fluorosurfactant and ZONYL®FSC and ZONYL® FSD, cationic fluorosurfactants; as well as fluorosurfactants marketed by The 3M Corporation under the FLUORAD® mark such as Fluorad® FC-171 (a nonionic fluorosurfactant), Fluorad® FC-135 (a cationic surfactant), Fluorad® FC-740 (generally described to be fluorinated alkyl esters), Fluorad® FC-430 (generally described to be fluorinated alkyl esters), Fluorad® FC-431 (generally described to be fluorinated alkyl esters), and, Fluorad® FC-I 70-C (generally described as being fluorinated alkyl polyoxyethylene ethanols);

(3) alkali metal salts of alkylbenzene and alkyl toluene sulfonic acids where alkyl has from about 9 to about 15 carbon atoms;

(4) alkali metal and amine, e.g. an ethanolamine, salts of mono- and di-alkyl esters of sulfosuccinic acid where alkyl can be straight or branched and has from 7 to 30 carbon atoms;

(5) alkali metal or ammonium salts of the reaction product of $C_8$ to $C_{22}$ alcohols and ethylene oxide. Specific useful surfactants include those described in WO 92/18100, namely ammonium laureth sulfate; parenth-15-7 carboxylic acid; TEA-oleamido PEG-n sulfosuccinate; and PPG-5-ceteth-10 phosphate;

(6) lauryl sulfates; oleyl succinates; lauryl ether sulfates; dodecylbenzene sulfonates; and N-lauroyl sarcosinate. The usual counter ion is sodium, ammonium or ethanolamines such as mono and triethanolamine;

(7) aminocarboxylic and aminosulfonic acids and salts thereof such as alkali metal 3-(dodecylamino) propionate and alkali metal 3-(dodecylamino) propane-1-sulfonate; and alkyl and alkylamido betaines such as cocamidopropyl betaine;

(8) $C_8$-$C_{18}$ alcohol ethoxylates including linear primary, and secondary alcohol ethoxylates [more preferably, a $C_{12-15}$ linear primary ethoxylate have 7 moles EO (ethylene oxide) per mole of alcohol, as commercially available under the trademark NEODOL™ 25-7 supplied by Shell Chemical Company, Houston, Tex.];

(9) nonionic surfactants in which the major portion of the molecule is made up of block polymeric $C_2$-$C_4$ alkylene oxides, with alkylene oxide blocks containing $C_3$ to $C_4$ alkylene oxides;

(10) nonionic surfactants which are the condensation products of a long chain ethylene oxide moiety with an aliphatic alcohol preferably a primary or secondary aliphatic alcohol or alkyl phenol, preferably the primary or secondary alcohol contains 8 to 20 carbon atoms and the alkyl phenol-based moiety is one wherein the alkyl chain is straight or branched and contains 6 to 12 carbon atoms, preferably 6 to 9 carbon atoms;

(11) The alkyl polyglycosides which can be used as nonionic surfactants in the composition are generally represented by formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6;

(12) nonionic surfactant compositions based on amine oxides including, e.g., (a) alkyl di (lower alkyl) amine oxides in which the alkyl group has about 10-20, and preferably 12-16 carbon atoms, and can be straight or branched chain, saturated or unsaturated, and the lower alkyl groups include between 1 and 7 carbon atoms, e.g., lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide, (b) alkyl di (hydroxy lower alkyl) amine oxides in which the alkyl group has about 10-20, and preferably 12-16 carbon atoms, which can be straight or branched chain, saturated or unsaturated, e.g., bis(2-hydroxyethyl) cocoamine oxide, bis(2-hydroxyethyl) tallowamine oxide; and bis(2-hydroxyethyl) stearylamine oxide, (c) alkylamidopropyl di(lower alkyl) amine oxides in which the alkyl group has about 10-20, and preferably 12-16 carbon atoms, and can be straight or branched chain, saturated or unsaturated, e.g., cocoamidopropyl dimethyl amine oxide and tallowamidopropyl dimethyl amine oxide; and (d) alkylmorpholine oxides in which the alkyl group has about 10-20, and preferably 12-16 carbon atoms, and can be straight or branched chain, saturated or unsaturated.

The compositions of the invention may be formulated with conventional propellants for dispensing as aerosols from conventional pressurized containers. Propellants which may be used are well known and conventional in the art and include, for example, a hydrocarbon, of from 1 to 10 carbon atoms, such as n-propane, n-butane, isobutane, n-pentane, isopentane, and mixtures thereof; dimethyl ether and blends thereof as well as individual or mixtures of chlorofluoro- and/or fluorohydrocarbons- and/or hydrochlorofluorocarbons (HCFCs). Useful commercially available hydrocarbon based propellant compositions include A-70 (Aerosol compositions with a vapor pressure of 70 psig available from companies such as Diversified and Aeropress.), as well as fluorocarbon based propellant compositions such as DYMEL 152A (commercially available from DuPont.) Compressed gases such as carbon dioxide, compressed air, nitrogen, and possibly dense or supercritical fluids may also be used.

The amount of propellant employed should provide a suitable spray pattern and for essentially complete expulsion of the composition from the aerosol container. The appropriate amount to be used for any particular aerosol propellant system can readily be determined by one skilled in the art. Preferably, the propellants comprise about 1% to about 50% of the aerosol formulation with preferred amounts being from about 2% to about 25%, more preferably from about 5% to about 15%. Generally speaking, the amount of a particular propellant employed should provide an internal pressure of from about 20 to about 150 psig at 70° F.

Preferred embodiments of the invention are ones in which the compositions are prepared with a propellant and supplied to the consumer in a pressurized vessel.

The inventors have found that the choice of propellant may advantageously affect the ultimate pH of the pressurized compositions. According to certain preferred embodiments wherein pressurized non-fluorocarbon and non-hydrocarbon gases are used, particularly carbon dioxide, compressed air, nitrogen and the like, the pressurized compositions are preferably adjusted to a pH of 10 or less, more preferably in excess of 7 to about 9, and most preferably in excess of about 7.5 to about 8.5. According to certain alternately preferred embodiments wherein pressurized hydrocarbons are used as the propellant, particularly non-fluorocarbon materials containing $C_1$-$C_{10}$ to 10 carbon atoms, such as n-propane, n-butane, isobutane, n-pentane, isopentane, and mixtures thereof; dimethyl ether and blends thereof and the like, the pressurized compositions are preferably adjusted to a pH of about 9.5 and greater, more preferably about 10 to about 13, and most preferably a pH in the range of about 10.5-12.

The compositions can be packaged in conventional, ready-to-use dispensing systems. Thus they can be packaged in aerosol form in conventional aerosol containers or in liquid form in non-aerosol trigger pumps spray bottles and squeeze bottles made from traditional and usual plastic materials such as polypropylene, polyethylene, and the like. They can also be impregnated into towelettes and packaged individually or packaged in bulk form for individual dispensing. can also be applied to a hard surface by using a wet wipe. The wipe can be of a woven or non-woven nature. Fabric substrates can include nonwoven or woven pouches, sponges, in the form of abrasive or non-abrasive cleaning pads. Such fabrics are known commercially in this field, and are often referred to as wipes. Such substrates can be resin bonded, hydroentanged, thermally bonded, meltblown, needlepunched or any combination of the former.

The nonwoven fabrics may be a combination of wood pulp fibers and textile length synthetic fibers formed by well known dry-form or wet-lay processes. Synthetic fibers such as rayon, nylon, orlon and polyester as well as blends thereof can be employed. The wood pulp fibers should comprise about 30 to about 60 percent by weight of the nonwoven fabric, preferably about 55 to about 60 percent by weight, the remainder being synthetic fibers. The wood pulp fibers provide for absorbency, abrasion and soil retention whereas the synthetic fibers provide for substrate strength and resiliency.

The substrate of the wipe may also be a film forming material such as a water soluble polymer. Such self-supporting film substrates may be sandwiched between layers of fabric substrates and heat sealed to form a useful substrate. The free standing films can be extruded utilizing standard equipment to devolatilize the blend. Casting technology can be used to form and dry films, or a liquid blend can be saturated into a carrier and then dried in a variety of known methods.

The compositions of the present invention are absorbed onto the wipe to form a saturated wipe. The wipe can then be sealed individually in a pouch which can then be opened when needed or a multitude of wipes can be placed in a container for use on an as-needed basis. The container, when closed, is sufficiently sealed to prevent evaporation of any components from the inventive compositions prior to their use. The inventive compositions may also be absorbed into a hydrophilic sponge article as well, which may find particular use in certain treatment methods.

The compositions can be prepared by entirely conventional procedures, e.g. by simple mixing of measured amounts of the required constituents and providing them to the ultimate container or substrate within which they are packaged for storage and ultimate use by a consumer.

The present invention also provides methods for the disinfecting treatment of hard surfaces wherein the presence of undesired microorganisms, e.g., gram positive type pathogenic bacteria or gram negative type pathogenic bacteria or viruses, particularly Poliovirus (type 1) is suspected, which process contemplates the step of applying an antimicrobially effective amount of a hard surface treatment composition described herein to the hard surfaces where the presence of undesired microorganisms is suspected.

The present invention also provides methods for the treatment of an ambient environment, particularly ambient air, which method contemplates the step of dispensing a composition according to the invention in an amount effective to exhibit antimicrobial efficacy against gram positive type pathogenic bacteria such as *Staphylococcus aureus*, and/or gram negative type pathogenic bacteria such as *Salmonella choleraesuis* and/or *Pseudomonas aeruginosa*. It is contemplated that according to such a method, the composition includes one or more glycols, particularly triethylene glycol as an essential constituent.

The following examples below illustrate exemplary formulations as well as preferred embodiments of the invention. It is to be understood that these examples are provided by way of illustration only and that further useful formulations falling within the scope of the present invention and the claims may be readily produced by one skilled in the art without deviating from the scope and spirit of the invention.

EXAMPLES

The following examples are presented for a further understanding of the invention. The data shown in Tables 1 through 5 show various embodiments of the present invention. Table 1 shows poliovirus inactivation at various levels of alcohol and pH; Table 2 demonstrates various comparative examples poliovirus inactivation at zero level alcohol at various pH; Tables 3A, 3B, and 3C show poliovirus inactivation at various alcohol levels at pH 7.0, 8.0, and 10.0, respectively; and Table 4 shows disinfection activity at various alcohol levels and pH.

TABLE 1

|  | Ex. 1 | Ex. 2 | Ex. 3 | Ex. 4 | Ex. 5 | Ex. 6 | Ex. 7 | Ex. 8 |
| --- | --- | --- | --- | --- | --- | --- | --- | --- |
| Ethyl alcohol | 45.00 | 45.00 | 45.00 | 45.00 | 45.00 | 55.00 | 55.00 | 55.00 |
| $Na_4EDTA$ (38%) | 1.50 | 1.50 | 1.50 | 1.50 | 1.50 | 1.50 | 1.50 | 1.50 |
| Citric acid (50%) | 0.11 | 0.08 | 0.06 | 0.04 | 0.03 | 0.35 | 0.24 | 0.20 |
| Deionized water | q.s. | q.s. | q.s. | q.s. | q.s. | q.s. | q.s. | q.s. |
| pH | 9.5 | 10.0 | 10.5 | 11.0 | 11.5 | 7.0 | 8.0 | 8.5 |
| Poliovirus- log reduction | 0.00 | 1.00 | 1.00 | 1.00 | 3.00 | 0.88 | 0.50 | 2.88 |
|  | Ex. 9 | Ex. 10 | Ex. 11 | Ex. 12 | Ex. 13 | Ex. 14 | Ex. 15 | Ex. 16 |
| Ethyl alcohol | 55.00 | 55.00 | 55.00 | 60.00 | 60.00 | 65.00 | 65.00 | 70.00 |
| $Na_4EDTA$ (38%) | 1.50 | 1.50 | 1.50 | 1.50 | 1.50 | 1.50 | 1.50 | 1.50 |
| Citric acid (50%) | 0.15 | 0.10 | 0.08 | 0.22 | 0.29 | 0.24 | 0.37 | 0.39 |
| Deionized water | q.s. | q.s. | q.s. | q.s. | q.s. | q.s. | q.s. | q.s. |
| pH | 9.0 | 9.5 | 10.0 | 7.5 | 8.0 | 7.0 | 8.0 | 7.0 |
| Poliovirus- log reduction | 4.50 | 4.17 | 4.88 | 1.33 | 2.00 | 2.33 | 2.67 | 4.67 |

TABLE 2

|  | Ex. 17 | Ex. 18 | Ex. 19 |
| --- | --- | --- | --- |
| Ethyl alcohol | — | — | — |
| $Na_4EDTA$ (38%) | 1.50 | 1.50 | 1.50 |
| Citric acid (50%) | 0.29 | 0.14 | — |
| Deionized water | q.s. | q.s. | q.s. |
| pH | 7.0 | 10.0 | 11.5 |
| Poliovirus- log reduction | 0.00 | 0.00 | 0.05 |

TABLE 3A

|  | Ex. 20 | Ex. 21 | Ex. 22 | Ex. 23 |
| --- | --- | --- | --- | --- |
| Ethyl alcohol | — | 55.00 | 65.00 | 70.00 |
| $Na_4EDTA$ (38%) | 1.50 | 1.50 | 1.50 | 1.50 |
| Citric acid (50%) | 0.29 | 0.35 | 0.24 | 0.39 |
| Deionized water | q.s. | q.s. | q.s. | q.s. |
| pH | 7.0 | 7.0 | 7.0 | 7.0 |
| Poliovirus- log reduction | 0.00 | 0.88 | 2.33 | 4.67 |

TABLE 3B

|  | Ex. 24 | Ex. 25 | Ex. 26 |
| --- | --- | --- | --- |
| Ethyl alcohol | 55.00 | 60.00 | 65.00 |
| $Na_4EDTA$ (38%) | 1.50 | 1.50 | 1.50 |
| Citric acid (50%) | 0.24 | 0.29 | 0.37 |
| Deionized water | q.s. | q.s. | q.s. |
| pH | 8.0 | 8.0 | 8.0 |
| Poliovirus- log reduction | 0.50 | 2.00 | 2.67 |

TABLE 3C

|  | Ex. 27 | Ex. 28 | Ex. 29 |
| --- | --- | --- | --- |
| Ethyl alcohol | — | 45.00 | 55.00 |
| $Na_4EDTA$ (38%) | 1.50 | 1.50 | 1.50 |
| Citric acid (50%) | 0.14 | 0.08 | 0.08 |
| Deionized water | q.s. | q.s. | q.s. |
| pH | 10.0 | 10.0 | 10.0 |
| Poliovirus- log reduction | 0.00 | 1.00 | 4.88 |

TABLE 4

|  | Ex. 30 | Ex. 31 | Ex. 32 | Ex. 33 |
| --- | --- | --- | --- | --- |
| Ethyl alcohol | 60.000 | 60.000 | 56.500 | 55.000 |
| Onyxide ® 3300** | — | 0.100 | 0.050 | 0.50 |
| Corrosion Inhibitor | 0.099 | 0.099 | 0.097 | 0.100 |
| $Na_4EDTA$ (38%) | 1.482 | 1.482 | 1.488 | 1.900 |
| Fragrance | 0.225 | 0.225 | — | — |
| Ammonium hydroxide (28%) | 0.247 | 0.247 | 0.193 | 0.190 |
| Propellant | 1.200 | 1.200 | 3.500 | 5.000 |
| Deionized water | q.s. | q.s. | q.s. | q.s. |
| pH | 10.4 | 10.6 | 10.2 | 10.8 |
| Poliovirus- log reduction | 6.00 | N.E. | N.E. | 5.50 |
| *Staphylococcus aureus* survival | 0/60* | 0/20* | N.E. | N.E. |
| *Pseudomonas aeruginosa* survival | 0/60* | 0/20* | N.E. | N.E. |
| *M. smegmatis* survival | 0/15* | N.E. | N.E. | N.E. |
| *Salmonella choleraesuis* | N.E. | 0/20* | N.E. | N.E. |
| *Mycobacterium terrae* | N.E. | N.E. | 0/20* | 0/20* |

*number of positive plates/number of tested plates
N.E. not evaluated
**alkyl dimethyl benzyl ammonium saccharinate (33%)

Other exemplary compositions which are contemplated under the present invention and which have activity against a variety of organisms are shown in Tables 5A to 5H shown below.

TABLE 5A

|  | Ex. 34 | Ex. 35 | Ex. 36 | Ex. 37 |
|---|---|---|---|---|
| Anhydrous Ethanol | 12.930 | 50.850 | 20.000 | 20.000 |
| Isopropanol | 50.850 | 12.930 | 20.000 | 20.000 |
| Ammonium Hydroxide 28% | 0.032 | 0.018 | 0.020 | 0.020 |
| Deionized water | 36.220 | 36.220 | 60.000 | 60.000 |
| Propellant present (Y/N) | N | N | N | N |
| pH | 11.96 | 9.07 | 8.57 | 8.68 |

TABLE 5B

|  | Ex. 38 | Ex. 39 | Ex. 40 | Ex. 41 |
|---|---|---|---|---|
| Anhydrous Ethanol | 12.930 | 20.000 | 20.000 | 50.850 |
| Isopropanol | 50.850 | 20.000 | 20.000 | 12.930 |
| Ammonium Hydroxide 28% | 0.002 | 0.036 | 0.028 | 0.330 |
| Deionized water | 36.220 | 60.000 | 60.000 | 36.220 |
| Propellant present (Y/N) | N | N | N | N |
| pH | 9.82 | 10.51 | 10.26 | 11.10 |

TABLE 5C

|  | Ex. 42 | Ex. 43 | Ex. 44 | Ex. 45 | Ex. 46 | Ex. 47 |
|---|---|---|---|---|---|---|
| Anhydrous Ethanol | 40.000 | 20.000 | 40.000 | 20.000 | 20.000 | 40.000 |
| Isopropanol |  | 20.000 | 40.000 | 20.000 | 20.000 | 0.000 |
| EDTA 38% | qs pH | qs pH | qs pH | qs pH | qs pH | qs pH |
| Deionized water | 60.000 | 60.000 | 20.000 | 60.000 | 60.000 | 60.000 |
| Propellant present (Y/N) | N | N | N | N | N | N |
| pH | 10.20 | 10.25 | 10.25 | 10.27 | 7.96 | 10.30 |

TABLE 5D

|  | Ex. 48 | Ex. 49 | Ex. 50 | Ex. 51 | Ex. 52 |
|---|---|---|---|---|---|
| Anhydrous Ethanol | 20.000 | 12.930 | 50.850 | 20.000 | 20.000 |
| Isopropanol | 20.000 | 50.850 | 12.930 | 20.000 | 20.000 |
| EDTA 38% | qs pH | qs pH | qs pH | qs pH | qs pH |
| Deionized water | 60.000 | 36.220 | 36.220 | 60.000 | 60.000 |
| Propellant present (Y/N) | N | N | N | N | N |
| pH | 12.46 | 11.46 | 9.06 | 10.20 | 10.15 |

"qs pH" = sufficient to provide the targeted pH

TABLE 5E

|  | Ex. 53 | Ex. 54 | Ex. 55 | Ex. 56 |
|---|---|---|---|---|
| Anhydrous Ethanol | 24.000 | 60.000 | 40.000 | 36.000 |
| Isopropanol | 16.000 | 0.000 | 0.000 | 24.000 |
| Sodium Hydroxide 1N | qs pH | qs pH | qs pH | qs pH |
| Deionized water | 60.000 | 40.000 | 60.000 | 40.000 |
| Propellant present (Y/N) | N | N | N | N |
| pH | 10.97 | 11.59 | 10.99 | 11.55 |

TABLE 5F

|  | Ex. 57 | Ex. 58 | Ex. 59 | Ex. 60 |
|---|---|---|---|---|
| Anhydrous Ethanol | 60.000 | 36.000 | 60.000 | 40.000 |
| Isopropanol | 0.000 | 24.000 | 0.000 | 10.000 |
| Sodium Hydroxide 1N | qs pH | qs pH | qs pH | qs pH |
| Deionized water | 40.000 | 40.000 | 40.000 | 50.000 |
| Propellant present (Y/N) | N | N | N | N |
| pH | 11.05 | 10.45 | 11.55 | 10.81 |

TABLE 5G

|  | Ex. 61 | Ex. 62 | Ex. 63 | Ex. 64 |
|---|---|---|---|---|
| Anhydrous Ethanol | 50.000 | 55.000 | 60.000 | 65.000 |
| Onyxide 3300 (33%) | 0.049 | 0.049 | 0.049 | 0.049 |
| Corrosion Inhibitor | 0.140 | 0.060 | 0.060 | 0.060 |
| Sodium benzoate | 0.098 | 0.098 | 0.098 | 0.098 |
| Ammonium Hydroxide 28% | 0.140 | 0.140 | 0.140 | 0.140 |
| Perfume | 0.225 | 0.225 | 0.225 | 0.225 |
| Deionized water | 42.349 | 37.428 | 32.428 | 27.428 |
| Propellant (carbon dioxide) | 7.000 | 7.000 | 7.000 | 7.000 |
| pH | 10.95 | 10.96 | 10.97 | 10.99 |

TABLE 5H

|  | Ex. 65 | Ex. 66 | Ex. 67 | Ex. 68 |
|---|---|---|---|---|
| Anhydrous Ethanol | 66.000 | 70.000 | 58.000 | 62.000 |
| Onyxide 3300 (33%) | 0.049 | 0.049 | 0.049 | 0.049 |
| Corrosion Inhibitor | 0.060 | 0.060 | 0.060 | 0.060 |
| Sodium benzoate | 0.098 | 0.098 | 0.098 | 0.098 |
| Sodium Hydroxide 1N | 0.093 | 0.093 | 0.093 | 0.093 |
| Ammonium Hydroxide 28% | 0.093 | 0.093 | 0.093 | 0.093 |
| Perfume | 0.225 | 0.225 | 0.225 | 0.225 |
| Deionized water | 26.381 | 22.381 | 34.382 | 30.381 |
| Propellant (carbon dioxide) | 7.000 | 7.000 | 7.000 | 7.000 |
| pH | 11.28 | 11.31 | 11.00 | 11.17 |

TABLE 5I

|  | Ex. 69 | Ex. 70 | Ex. 71 | Ex. 72 | Ex. 73 | Ex. 74 | Ex. 75 | Ex. 76 |
|---|---|---|---|---|---|---|---|---|
| Anhydrous Ethanol | 58.00 | 65.00 | 60.00 | 63.00 | 55.00 | 66.00 | 70.00 | 58.00 |
| Onyxide 3300 (33%) | 0.30 | 0.30 | 0.30 | 0.304 | 0.304 | 0.15 | 0.15 | 0.15 |
| Corrosion Inhibitor | 0.06 | 0.06 | 0.063 | 0.063 | 0.063 | 0.06 | 0.06 | 0.06 |
| Sodium benzoate | 0.10 | 0.10 | 0.102 | 0.102 | 0.102 | 0.098 | 0.098 | 0.098 |
| Sodium Hydroxide 1N | — | — | — | — | — | 0.093 | 0.093 | 0.093 |
| Ammonium Hydroxide | 0.10 | 0.10 | 0.097 | 0.097 | 0.097 | 0.093 | 0.093 | 0.093 |
| sodium EDTA | 1.00 | 1.00 | 1.00 | 1.00 | 1.00 | — | — | — |
| Deionized water | 33.44 | 30.13 | 23.43 | 28.43 | 36.43 | 26.38 | 22.38 | 34.38 |

TABLE 5I-continued

|  | | | | | | | |
|---|---|---|---|---|---|---|---|
| Propellant[A] | — | 3.30 | — | — | — | — | — | — |
| Propellant[B] | 7.00 | — | — | 7.00 | 7.00 | 7.00 | 7.00 | 7.00 |
| Propellant[C] | — | — | 15.00 | — | — | — | — | — |
| pH | 10.6 | 11.93 | 12.48 | 11.95 | 11.82 | 10.84 | 10.70 | 10.49 |

|  | Ex. 77 | Ex. 78 | Ex. 79 | Ex. 80 | Ex. 81 | Ex. 82 | Ex. 83 |
|---|---|---|---|---|---|---|---|
| Anhydrous Ethanol | 62.00 | 62.00 | 66.00 | 58.00 | 70.00 | 66.00 | 70.00 |
| Onyxide 3300 (33%) | 0.15 | 0.15 | 0.15 | 0.15 | 0.15 | 0.15 | 0.15 |
| Corrosion Inhibitor | 0.06 | 0.06 | 0.06 | 0.06 | 0.06 | 0.06 | 0.06 |
| Sodium benzoate | 0.098 | 0.098 | 0.098 | 0.098 | 0.098 | 0.098 | 0.098 |
| Sodium Hydroxide 1N | 0.093 | 0.093 | 0.093 | 0.093 | 0.093 | 0.093 | 0.093 |
| Ammonium Hydroxide | 0.093 | 0.093 | 0.093 | 0.093 | 0.093 | 0.093 | 0.093 |
| sodium EDTA | — | — | — | — | — | — | — |
| Deionized water | 30.38 | 30.38 | 26.38 | 34.38 | 22.38 | 26.38 | 22.38 |
| Propellant[A] | — | — | — | — | — | — | — |
| Propellant[B] | 7.00 | 7.00 | 7.00 | 7.00 | 7.00 | 7.00 | 7.00 |
| Propellant[C] | — | — | — | — | — | — | — |
| pH | 10.50 | 10.53 | 10.60 | 10.46 | 10.68 | 11.43 | 11.57 |

|  | Ex. 84 | Ex. 85 | Ex. 86 | Ex. 87 | Ex. 88 | Ex. 89 | Ex. 90 | Ex. 91 |
|---|---|---|---|---|---|---|---|---|
| Anhydrous Ethanol | 58.00 | 66.00 | 62.00 | 62.00 | 58.00 | 70.00 | 66.00 | 58.00 |
| Onyxide 3300 (33%) | 0.15 | 0.15 | 0.15 | 0.15 | 0.15 | 0.15 | 0.15 | 0.15 |
| Corrosion Inhibitor | 0.06 | 0.06 | 0.06 | 0.06 | 0.06 | 0.06 | 0.06 | 0.06 |
| Sodium benzoate | 0.098 | 0.098 | 0.098 | 0.098 | 0.098 | 0.098 | 0.098 | 0.098 |
| Sodium Hydroxide 1N | 0.093 | 0.093 | 0.093 | 0.093 | 0.093 | 0.093 | 0.093 | 0.093 |
| Ammonium Hydroxide | 0.093 | 0.093 | 0.093 | 0.093 | 0.093 | 0.093 | 0.093 | 0.093 |
| Deionized water | 34.38 | 26.38 | 30.38 | 30.38 | 34.38 | 22.38 | 26.38 | 34.38 |
| Propellant[B] | 7.00 | 7.00 | 7.00 | 7.00 | 7.00 | 7.00 | 7.00 | 7.00 |
| pH | 11.13 | 11.32 | 11.27 | 11.29 | 11.16 | 11.55 | 11.36 | 11.11 |

|  | Ex. 92 | Ex. 93 | Ex. 94 | Ex. 95 | Ex. 96 | Ex. 97 |
|---|---|---|---|---|---|---|
| Anhydrous Ethanol | 66.00 | 70.00 | 62.00 | 70.00 | 62.00 | 58.00 |
| Onyxide 3300 (33%) | 0.15 | 0.15 | 0.15 | 0.15 | 0.15 | 0.15 |
| Corrosion Inhibitor | 0.06 | 0.06 | 0.06 | 0.06 | 0.06 | 0.06 |
| Sodium benzoate | 0.098 | 0.098 | 0.098 | 0.098 | 0.098 | 0.098 |
| Sodium Hydroxide 1N | 0.093 | 0.093 | 0.093 | 0.093 | 0.093 | 0.093 |
| Ammonium Hydroxide | 0.093 | 0.093 | 0.093 | 0.093 | 0.093 | 0.093 |
| Deionized water | 26.38 | 22.38 | 30.38 | 22.38 | 30.38 | 34.38 |
| Propellant[B] | 7.00 | 7.00 | 7.00 | 7.00 | 7.00 | 7.00 |
| pH | 11.38 | 11.53 | 11.09 | 11.44 | 11.18 | 11.00 |

|  | Ex. 98 | Ex. 99 | Ex. 100 | Ex. 101 |
|---|---|---|---|---|
| Anhydrous Ethanol | 55.0 | 54.9 | 58.0 | 62.0 |
| Onyxide 3300 (33%) | — | 0.152 | 0.304 | 0.15 |
| Corrosion Inhibitor | 0.071[D] | 0.071[D] | 0.063[E] | 0.06[E] |
| Sodium benzoate | — | — | 0.102 | 0.098 |
| Sodium Hydroxide 1N | — | — | — | 0.093 |
| Ammonium Hydroxide | 0.19 | 0.19 | 0.097 | 0.093 |
| sodium EDTA | 0.98 | — | 1.0 | — |

TABLE 5I-continued

| | | | | |
|---|---|---|---|---|
| Deionized water | 38.63 | 39.37 | 28.43 | 30.38 |
| Propellant[B] | 5 | 5 | 7 | 7 |
| pH | 10.43 | 10.6 | 11.88 | 11.29 |

Propellant[A] = carbon dioxide
Propellant[B] = hydrocarbon propellant
Propellant[C] = DYMEL 152a flurorocarbon propellant (ex. DuPont)
[D]Monofax 939 = phosphate ester
[E]Monacor BE = mixed monoethanolamine borate and monoisopropanol borate Evaluation of Antimicrobial Efficacy:

Certain formulations indicated on the following Tables 6A-6D according to the invention contained in a PVOH pouch were diluted in 945 mL of water to form a 1:64 dilution which were evaluated for their antimicrobial efficacy against one or more of: *Salmonella choleraesuis* (ATCC 10708), *Staphylococcus aureus* (ATCC 6538), *Escherichia coli* (ATCC 10536), *Pseudomonas aeruginosa* (ATCC 15442), Entercoccus hirae (ATCC 10541), *Aspergillus niger* (ATCC 6275), *T. mentagrophytes* (ATCC 9533), Hepatitis A (strain acquired from a university resource), Poliovirus Type 1 (P01, ATCC VR-192, or ATCC VR-1000, strain Brunhilde), Coxsachievirus (ATCC VR-30), Rotavirus (Wa strain, ATCC VR-2018), and/or Rhinovirus (Rhinovirus Type 39, ATCC VR-340).

The method for determining the efficacy of various Example formulations recited above against specific microorganisms was generally in accordance with one or more of the protocols. The method for determining the efficacy of various formulations against the bacteria mentioned above was based on the standard ASTM E 1153-87 Standard Test Method for Efficacy of Sanitizers Recommended for Inanimate Non-Food Contact Surfaces, EPA—Virucidal Test Method as specified in the US EPA Pesticide Assessment Guidelines Subdivision G: Product Performance 91-2(f) Products for Use on Hard Surfaces, or AOAC Germicidal Spray Products Test or the AOAC Tuberculocidal Activity of Disinfectant Spray Products Test. A representative film of target bacteria or other microorganism was dried on a hard, non-porous surface (e.g., glass slide). The treated slides were then treated with the test formulations for a contact time of ten minutes. After exposure, the treated slides were transferred to vessels containing neutralizing media and assayed for survivors. Appropriate viability, dried organism population and neutralization controls were conducted.

TABLE 6A

| | 30 second contact time | |
|---|---|---|
| Example: | Challenge Organism: | log reduction |
| 70 | Rotavirus | 3.83 |
| 71 | Rotavirus | 3.83 |
| 72 | Rotavirus | 3.83 |
| 70 | Rhinovirus | 3 |
| 71 | Rhinovirus | 3 |
| 72 | Rhinovirus | 3 |
| 72 | *Staphylococcus aureus* | 5.3 |
| 72 | *Enterobacter aerogenes* | 4 |

With reference to Table 6A, the evaluation of efficacy against Rotavirus and Rhinovirus was performed in accordance with the protocol outlined in the EPA—Virucidal Test Method, noted supra. With further reference to Table 6A, evaluation of efficacy against *Staphylococcus aureus* and *Enterobacter aerogenes* was performed in accordance with the AOAC Germicidal Spray Test based on the ASTM E 1153-87 defined protocol. All of the formulations demonstrate good antimicrobial efficacy against the challenge organisms.

TABLE 6B

| | 10 minute contact time | |
|---|---|---|
| Example: | Challenge Organism: | log reduction |
| 76 | hepatitis A | >5 |
| 80 | hepatitis A | >5 |
| 78 | hepatitis A | >5 |
| 74 | hepatitis A | >5 |
| 79 | hepatitis A | >5 |
| 75 | hepatitis A | >5 |
| 81 | hepatitis A | >5 |
| 88 | hepatitis A | >6 |
| 97 | hepatitis A | >6 |
| 87 | hepatitis A | >6 |
| 88 | hepatitis A | >6 |
| 94 | hepatitis A | >5.5 |
| 90 | hepatitis A | >6 |
| 89 | hepatitis A | >6 |
| 95 | hepatitis A | >6 |
| 93 | hepatitis A | >5.5 |
| 89 | hepatitis A | >4 |
| 95 | hepatitis A | >3.5 |
| 72 | hepatitis A | >5 |
| 71 | hepatitis A | >5 |
| 69 | hepatitis A | >5 |

With reference to Table 6B, the evaluation of efficacy against the Hepatitis A virus was performed in accordance with the protocol outlined in the EPA—Virucidal Test Method, noted supra. All of the formulations demonstrate excellent antimicrobial efficacy against the Hepatitis A virus.

TABLE 6C

| | 10 minute contact time | |
|---|---|---|
| Example: | Challenge Organism: | log reduction |
| 84 | Polio | >4.75 |
| 88 | Polio | >5 |
| 89 | Polio | >4.5 |
| 91 | Polio | >4 |
| 86 | Polio | >4.75 |
| 87 | Polio | >5 |
| 96 | Polio | >4.5 |
| 94 | Polio | >4 |
| 85 | Polio | >4.75 |
| 82 | Polio | >5 |
| 90 | Polio | >4.5 |
| 92 | Polio | >4 |
| 92 | Polio | >5.5 |
| 83 | Polio | >4.75 |
| 89 | Polio | >5 |
| 95 | Polio | >4.5 |
| 93 | Polio | >4 |
| 89 | Polio | >4.5 |
| 95 | Polio | >5.5 |

TABLE 6C-continued

| | 10 minute contact time | |
|---|---|---|
| Example: | Challenge Organism: | log reduction |
| 72 | Polio | >4.5 |
| 71 | Polio | >4.5 |
| 69 | Polio | >4.5 |

W
With reference to Table 6C, the evaluation of efficacy against Polio (Type 1) virus was performed in accordance with the protocol outlined in the EPA—Virucidal Test Method, noted supra. All of the formulations demonstrate excellent antimicrobial efficacy against the tested Polio (Type 1) virus.

TABLE 6D

| | 10 minute contact time | |
|---|---|---|
| Example: | Challenge Organism: | log reduction |
| 84 | coxsachievirus | >5 |
| 97 | coxsachievirus | >5.5 |
| 86 | coxsachievirus | >5 |
| 87 | coxsachievirus | >4.25 |
| 96 | coxsachievirus | >5.5 |
| 94 | coxsachievirus | >4.25 |
| 85 | coxsachievirus | >5 |
| 82 | coxsachievirus | >4.25 |
| 90 | coxsachievirus | >5.5 |
| 92 | coxsachievirus | >4.25 |
| 83 | coxsachievirus | >5 |
| 89 | coxsachievirus | >4.25 |
| 95 | coxsachievirus | >5.5 |
| 93 | coxsachievirus | >4.25 |

With reference to Table 6D, the evaluation of efficacy against the Coxsachievirus virus was performed in accordance with the protocol outlined in the EPA—Virucidal Test Method, noted supra. All of the formulations demonstrated excellent antimicrobial efficacy against the tested Coxsachievirus.

TABLE 6E

| | 10 minute contact time | |
|---|---|---|
| Example: | Challenge Organism: | plate count |
| 98 | *Staphylococcus aureus* | 0/60 |
| 72 | *Staphylococcus aureus* | 0/30 |
| 99 | *Salmonella choleraesuis* | 0/20 |
| 98 | *Pseudomonas aeruginosa* | 0/60 |
| 99 | *Pseudomonas aeruginosa* | 0/40, 1/20 |
| 72 | *Aspergillus niger* | 0/10 |
| 72 | *Salmonella choleraesuis* | 0/30 |

With reference to Table 6E, evaluation of efficacy against *Staphylococcus aureus, Salmonella* choleraesuis, *Pseudomonas aeruginosa* and *Aspergillus niger* was performed in accordance with the AOAC Germicidal Spray Test based on the ASTM E 1153-87 defined protocol. All of the tested formulations demonstrates good antimicrobial efficacy against the challenge organisms.

The invention claimed is:

1. A hard surface treatment composition which is effective in providing reduction of Poliovirus (Type I) comprising:
    (a) 40%-70% wt. of an alcohol constituent selected from the group consisting of methanol, ethanol, n-propanol, isopropanol, n-butanol, benzyl alcohol, and mixtures thereof;
    (b) 0.01-5% wt. of an effective amount of a pH adjusting agent such that the pH range of the composition is 10 or greater;
    (c) water to provide to 100% wt. of the composition; and,
    0.01-0.1% wt a non-chloride ion containing quaternary ammonium antimicrobial having antimicrobial properties as an antimicrobial constituent
    (d) optionally, one or more further constituents selected from the group consisting of further antimicrobials, corrosion inhibitors, perfumes, perfume carriers, deodorants, organic solvents, surfactants, propellants, pH buffers, organic acids, fungicides, and anti-oxidants;
    characterized in that the constituents (a), (b) and (c) in the absence of (d) exhibit a reduction of at least 1 $\log_{10}$ of Poliovirus (Type I).

2. The composition according to claim 1 wherein the amount of alcohol is from about 50 to about 70 weight percent.

3. The composition according to claim 2 wherein the amount of alcohol is from about 50 to about 60 weight percent.

4. The composition according to claim 1 wherein the pH of the composition is from about 10.5 to about 13.

5. The composition according to claim 1 the alcohol is selected from ethanol, isopropanol, and mixtures thereof.

6. The composition according to claim 5 wherein the alcohol is ethanol.

7. A hard surface treatment compositions according to claim 1 which additionally comprises a propellant.

8. The composition according to claim 7 wherein the amount of alcohol is from about 50 to about 70 weight percent.

9. The composition according to claim 8 wherein the amount of alcohol is from about 50 to about 60 weight percent.

10. The composition according to claim 7 wherein the pH of the composition is from about 10.5 to about 13.

11. The composition according to claim 7 the alcohol is selected from ethanol, isopropanol, and mixtures thereof.

12. The composition according to claim 11 wherein the alcohol is ethanol.

13. A hard surface treatment composition according to claim 1 characterized in that the hard surface treatment composition exhibits antimicrobial efficacy against one or more of: *Entercoccus hirae , Aspergillus niger, T mentagrophytes*, Hepatitis A, Coxsachievirus , Rotavirus, or Rhinovirus.

14. A process for providing a disinfecting treatment of hard surfaces wherein the presence of one or more undesired microorganisms is suspected, which process comprises the step of:
    applying an antimicrobially effective amount of a hard surface treatment composition according to claim 1 to the hard surfaces where the presence of undesired microorganisms selected from one or more of: *Salmonella choleraesuis, Staphylococcus aureus, Escherichia coli, Pseudomonas aeruginosa, Entercoccus hirae , Aspergillus niger, T mentagrophytes*, Hepatitis A , Poliovirus Type 1, Coxsachievirus , Rotavirus, or Rhinovirus is suspected.

15. A process for providing a disinfecting treatment of hard surfaces wherein the presence of one or more undesired microorganisms is suspected, which process comprises the step of:
    applying an antimicrobially effective amount of a hard surface treatment composition according to claim 7 to the hard surfaces where the presence of undesired microorganisms selected from one or more of: *Salmo-* nella choleraesuis, Staphylococcus aureus, Escherichia coli, Pseudomonas aeruginosa, Entercoccus hirae, Aspergillus niger, T. mentagrophytes, Hepatitis A, Poliovirus Type 1, Coxsachievirus, Rotavirus, or Rhinovirus is suspected.

16. A method for treating ambient air which method comprises the step of:

dispensing an effective amount of a hard surface composition according to claim 1 in an amount effective to exhibit antimicrobial efficacy against gram positive type pathogenic bacteria and/or gram negative type bacteria.

17. A method for treating ambient air which method comprises the step of:

dispensing an effective amount of a hard surface composition according to claim 7 in an amount effective to exhibit antimicrobial efficacy against gram positive type pathogenic bacteria and/or gram negative type bacteria.

\* \* \* \* \*

UNITED STATES PATENT AND TRADEMARK OFFICE
CERTIFICATE OF CORRECTION

PATENT NO. : 8,877,698 B2  
APPLICATION NO. : 12/783982  
DATED : November 4, 2014  
INVENTOR(S) : Mark Timothy Bennett et al.

Page 1 of 1

It is certified that error appears in the above-identified patent and that said Letters Patent is hereby corrected as shown below:

Title page, item (63), and in the Specification, col. 1, line 4-7,

"Continuation of application No. 10/645,248, filed in Aug. 20, 2003, now Pat. No. 7,915,210, which is a continuation-in-part of application No. PCT/GB02/00357, filed on Jan. 25, 2002." should read -- "Continuation of application No. 10/645,248, filed in Aug. 20, 2003, now Pat. No. 7,915,210, which is a continuation-in-part of application No. PCT/GB02/00357, filed on Jan. 28, 2002." --

Signed and Sealed this  
First Day of March, 2016

Michelle K. Lee  
*Director of the United States Patent and Trademark Office*